US006273875B1

United States Patent
Siman et al.

(10) Patent No.: US 6,273,875 B1
(45) Date of Patent: Aug. 14, 2001

(54) MEDICAL DEVICES HAVING IMPROVED ANTIMICROBIAL/ANTITHROMBOGENIC PROPERTIES

(75) Inventors: Jaime Siman; Jeff Dove, both of Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/135,873

(22) Filed: Aug. 17, 1998

(51) Int. Cl.[7] .......................... A61M 25/00; A61M 5/32; A01N 1/00
(52) U.S. Cl. .................. 604/264; 604/265; 604/266; 604/523; 604/20; 523/112
(58) Field of Search .................. 604/264–66, 20–21, 604/523; 523/112; 623/1; 428/35.7, 36.9; 424/422

(56) References Cited

U.S. PATENT DOCUMENTS

| 3,988,782 | 11/1976 | Dardik et al. . |
| 4,054,139 | 10/1977 | Crossley ................................. 128/260 |
| 4,476,590 | 10/1984 | Scales et al. . |
| 4,603,152 | 7/1986 | Laurin et al. . |
| 4,786,556 | * 11/1988 | Hu et al. ................................. 438/412 |
| 4,846,844 | 7/1989 | De Leon et al. . |
| 4,917,686 | 4/1990 | Bayston et al. . |
| 4,999,210 | * 3/1991 | Solomon et al. ........................ 427/2 |
| 5,019,096 | 5/1991 | Fox, Jr. et al. . |
| 5,069,899 | 12/1991 | Whitbourne et al. ................... 424/56 |
| 5,165,952 | 11/1992 | Solomon et al. . |
| 5,217,493 | 6/1993 | Raad et al. . |
| 5,322,520 | 6/1994 | Milder . |
| 5,336,518 | * 8/1994 | Narayanan et al. ..................... 623/1 |
| 5,409,966 | 4/1995 | Duan et al. ........................... 522/167 |
| 5,411,527 | * 5/1995 | Alt ........................................... 607/5 |
| 5,468,562 | 11/1995 | Farivar et al. . |
| 5,474,797 | 12/1995 | Sioshansi et al. . |
| 5,498,248 | 3/1996 | Milder . |
| 5,516,480 | * 5/1996 | Krall et al. ............................ 264/343 |
| 5,520,664 | 5/1996 | Bricault, Jr. et al. . |
| 5,562,009 | * 10/1996 | Cohen et al. ..................... 128/662.02 |
| 5,567,495 | * 10/1996 | Modak et al. ........................ 428/36.9 |
| 5,609,629 | 3/1997 | Fearnot et al. ............................ 623/1 |
| 5,620,738 | 4/1997 | Fan et al. ............................... 427/2.3 |
| 5,642,855 | 7/1997 | Lorenz ................................... 424/449 |
| 5,741,224 | * 4/1998 | Milder et al. ............................ 604/20 |
| 5,756,145 | 5/1998 | Darouiche . |

(List continued on next page.)

FOREIGN PATENT DOCUMENTS 0379269    7/1990  (EP) .

*Primary Examiner*—Angela D. Sykes
*Assistant Examiner*—Patricia Bianco
(74) *Attorney, Agent, or Firm*—Lena I. Vinitskaya; Guy Cumberbatch

(57) ABSTRACT

An enhanced antimicrobial antithrombogenic medical device is formed by using an oligodynamic metal and a noble metal with a polymer, and forming the mixture into a device. By using low concentrations of conductive polymers or ionophoric compounds, non-conductive, or highly plasticized polymers can be likewise blended into an iontophoretic-capable composition. The surface of the device may be treated with a solvent to remove the top surface of the polymer and create surface voids in the composition in order to expose previously encapsulated iontophoretic materials. This surface treatment results in a larger reaction area of the iontophoretic capable composition that produces larger yields of bacteriostatic oligodynamic ions for a longer duration thereby increasing the antimicrobial effectiveness of the composition. The surface of the antimicrobial composition may be treated with an anticoagulant such as heparin or heparin complexed with a quaternary ammonium salt for an added bacteriostatic effect.

22 Claims, 2 Drawing Sheets

U.S. PATENT DOCUMENTS

| | | |
|---|---|---|
| 5,759,564 | 6/1998 | Milder et al. . |
| 5,772,640 * | 6/1998 | Modak et al. .................. 604/265 |
| 5,840,338 * | 11/1998 | Roos et al. ..................... 424/488 |
| 5,843,186 * | 12/1998 | Christ . |
| 5,846,558 * | 12/1998 | Nielsen et al. ................. 424/448 |
| 5,848,995 * | 12/1998 | Walder .......................... 604/265 |
| 5,967,714 * | 10/1999 | Ottersbach et al. ........... 408/424.2 |
| 6,033,582 * | 3/2000 | Lee et al. ........................ 216/37 |
| 6,080,490 * | 6/2000 | Burrell et al. . |
| 6,106,505 * | 8/2000 | Modak et al. . |

* cited by examiner

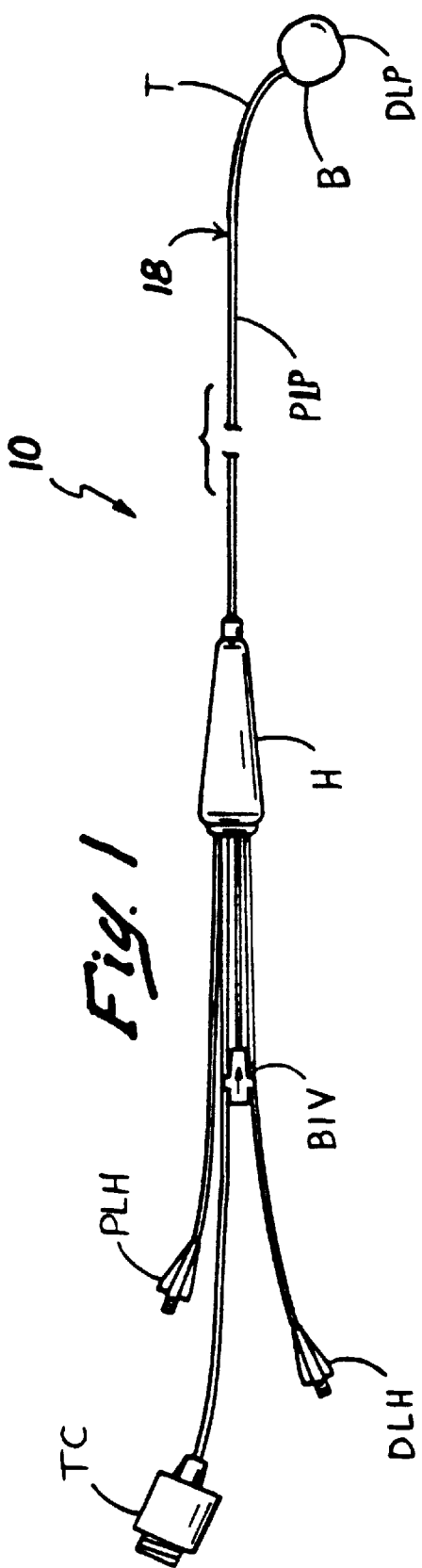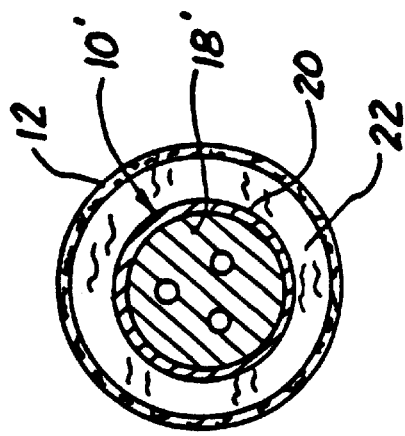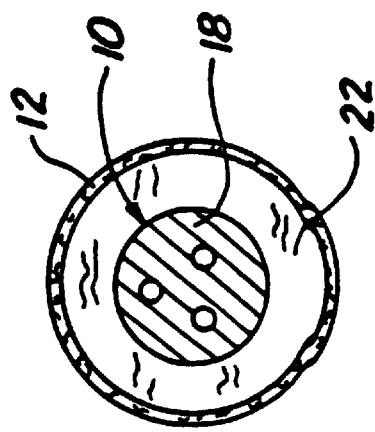

MEDICAL DEVICES HAVING IMPROVED ANTIMICROBIAL/ANTITHROMBOGENIC PROPERTIES

FIELD OF THE INVENTION

The present invention relates to medical devices which come into contact with human fluids such as catheters, obturators, implants, artificial hearts, dialysis tubes and similar devices, having improved antimicrobial/antithrombogenic properties, and, more particularly, to surface treatments of materials to enhance existing antimicrobial properties and introduce antithrombogenic properties.

BACKGROUND OF THE INVENTION

Continuing advancements in medicine have increased the use of synthetic materials that come into direct contact with blood and other physiological fluids. Synthetic materials have been used in many areas of medical treatment including artificial ocular lenses, heart valves, bypass tubes, implants, shunts, dialysis machines, catheters and other blood and fluid contacting devices or apparatus. Although the synthetic materials used to manufacture medical devices are mechanically stable and chemically inert, these synthetic materials are generally not biocompatible when exposed to bodily fluids such as blood.

Biocompatibility involves a number of parameters related to how the medical device interacts with the host. Undesirable physiological reactions such as thrombosis, which is the formation of blood clots, or bacterial infection may result because the synthetic materials of which medical devices are manufactured cause proteins and other physiological fluid components to adhere to their surfaces. The more prolonged the contact, the more likely infection and thrombosis will occur.

Thrombosis is the body's natural mechanism to prevent uncontrollable bleeding whenever the lining of the vasculature is disturbed. The introduction of medical devices sometimes initiates this natural defense mechanism. In addition, the synthetic surface of many medical devices may exacerbate the thrombogenic response. A thrombus, or a portion of a thrombus, may break free and travel throughout the vascular system, potentially causing serious problems downstream.

Substantial research and development has been undertaken to control, if not eliminate, infection and thrombogenesis caused by medical devices. The vast majority of metals and synthetic polymers used to manufacture medical devices do not have antimicrobial or antithrombogenic capabilities of their own. Consequently, most measures undertaken for creating antimicrobial and antithrombogenic devices involve either the addition of some component or the application of a covering to the synthetic material of the medical device. For example, a common precaution to prevent thrombus formation is to treat the medical device surface with an anticoagulant substance such as heparin or with heparin reacted with a quaternary ammonium compound. Heparin interferes with the coagulation cascade, thereby inhibiting thrombus formation.

Certain oligodynamic metals, such as silver, are well known to have an antiseptic action, and have been mixed with a dissimilar noble metal, such as platinum, and embedded in a polymer that is loaded with a conductive material such as carbon black. When this polymer comes into contact with the electrolytic bodily fluids of a patient, a galvanic current flow is produced through the conductive material between the two metals, causing ions of the oligodynamic metal to be released into the body. For example, the silver acts as a sacrificial electrode in the circuit giving off silver ions that are bacteriostatic and can stop the growth of bacteria on the surface of the medical device. Medical devices incorporating this technology are shown and described in WO 97/38648, and materials made thereby are termed iontophoretic.

Plasticized polymers, such as polyvinyl chloride (PVC), are common for use in tubing for various medical machines and devices, such as heart and lung machines and dialysis machines, and in the manufacture of catheters, due to desirable attributes such as greater flexibility and tensile strength. Loading a polymeric material with high levels of a conductive material, such as carbon black, to complete a galvanic circuit between embedded oligodynamic and noble metals is not possible for highly plasticized polymers, since a large percentage of the material is the nonconductive, oily plasticizer. The carbon black particles must be loaded at such high concentrations that they physically touch, which would change the entire nature of the plasticized polymer and decrease or eliminate many of its desired attributes.

In summary, there are several previously disclosed antimicrobial, antithrombogenic and combined antimicrobial/antithrombogenic coatings for medical devices. While these coatings achieve the desired effect of preventing blood clot formation, or thrombogenesis, and infection from insertion and use of the medical device within the human body, each of the disclosed methods has various limitations.

SUMMARY OF THE INVENTION

In accordance with the present invention, it was discovered that a number of enhancements could be made to improve the antimicrobial and antithrombogenic properties of medical devices used within the body. As will be set forth below, two basic areas of improvement are provided which can be used alone or in combination to improve the capabilities of these medical devices.

As a first feature of the present invention, it was discovered that the effectiveness of the active ingredients used to provide antithrombogenic properties can be enhanced by treating the surface of the medical device with a suitable solvent which penetrates the device surface and removes polymer material to expose active ingredients which would otherwise remain embedded within the device and inactive. By exposing additional active ingredients prior to implantation, the present invention provides medical devices having antithrombogenic protection which begins sooner after implantation and lasts longer.

A second feature of the present invention involves the discovery that the conductivity of polymers which are used in medical devices that include iontophoretic compounds can be enhanced by adding ionophores to the polymers. This aspect of the invention may be used to increase the conductivity of iontophoretic polymers which have inherent conductivity or it may be used to add necessary levels of conductivity to plasticized non-conductive polymers, such as polyvinyl chloride, which previously have not been used as a matrix for iontophoretic compounds. As a further feature, certain conductive polymers where also found to be effective in providing plasticized polymers with the levels of conductivity necessary to allow use of iontophoretic compounds with such polymers.

As an additional feature of the present invention, medical devices may be made which incorporate one or both of the above-described aspects of the invention. Additional features and attendant advantages of the present invention will become better understood when taken in conjunction with the accompanying detailed description and drawings.

DESCRIPTION OF THE DRAWINGS

FIG. 1 is a perspective view of a medical device, specifically a catheter, produced in accordance with the principles of the present invention;

FIG. 2 is a cross-sectional view of a medical device of the present invention positioned within a blood vessel;

FIG. 3 is a cross-sectional view similar to that of FIG. 2, particularly illustrating a medical device formed by coating the medical device with an antithrombogenic composition;

FIG. 4b is an enlarged cross-sectional view of one side of the catheter of FIG. 4a.

DETAILED DESCRIPTION OF THE INVENTION

Figure 4A:
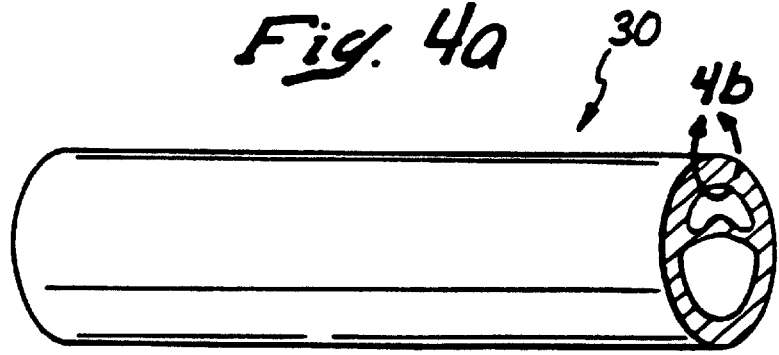
FIG. 4a is a perspective view of a multi-lumen catheter of the present invention.

Referring to the drawings in more detail, a medical device possessing antimicrobial and antithrombogenic properties of the present invention is illustrated in FIG. 1. The exemplary medical device is a catheter 10 having an elongate catheter body CB for insertion in a patient and a plurality of proximal tubes connected to the catheter body at a junction hub H. The catheter body CB may terminate in an inflatable balloon B supplied with inflation fluid/gas via a balloon inflation valve BIV. A distal lumen port DLP on the end of the catheter body CB is in fluid communication with a distal lumen hub DLH. A proximal lumen port PLP in the side wall of the catheter, typically about 30 cm from the distal lumen port DLP, is in fluid communication with a proximal lumen hub PLH. Finally, a thermistor T transmits signals to a thermistor connector TC. The construction of the catheter body CB is one application for the material composition of the present invention use, the catheter 10 may be positioned within a blood vessel (for example, a femoral artery) through an incision of a patient. Exemplary catheter 10 desirably possesses antimicrobial and antithrombogenic properties that significantly reduce or eliminate microbial infections and thrombus (blood clot) formation associated with its use.

To illustrate the antimicrobial and antithrombogenic properties of the medical devices of the present invention, reference is made to FIGS. 2 and 3 which respectively illustrate preferred embodiments of the catheter 10 within a blood vessel 12. In FIG. 2, the catheter 10 includes a body 18 made from a polymer which possesses antimicrobial and antithrombogenic properties. In FIG. 3, a catheter 10' is formed by coating its body 18' with an antimicrobial and antithrombogenic polymer coating 20. As shown by FIGS. 2 and 3, the polymers may be used as a coating for the medical device or they can actually form part or all of the device. In either case, the material forms a polymer body having a surface under which is located a polymer matrix that forms the bulk of the polymer body. Antimicrobial and antithrombogenic polymers and compositions of the present invention will be discussed in more detail below.

As discussed above, blood is an electrolytic fluid which initiates the iontophoretic action of the catheters 10 and 10'. Such materials and technology are known. See WO/9738648, the contents of which are hereby incorporated by reference. There may be a limitation on the reaction for such devices in which the galvanic metals are embedded within the polymer matrix, as opposed to being coated on the surface thereof. In particular, many catheters made with iontophoretic properties are extruded of a single doped polymer, with the iontophoretic reaction being initially limited based on the amount of galvanic components actually on the surface of the catheter. In other words, much of the galvanic material is embedded within the catheter walls, and unable to directly interact with the electrolytic blood.

Enhanced Iontophoretic Effect

Figure 4B:
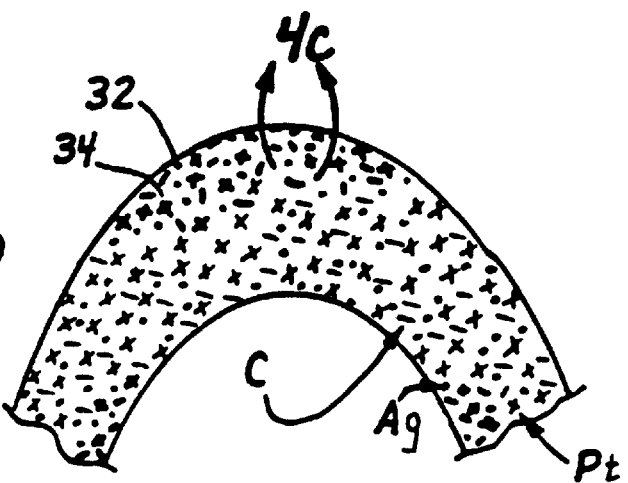
Figure 4C:
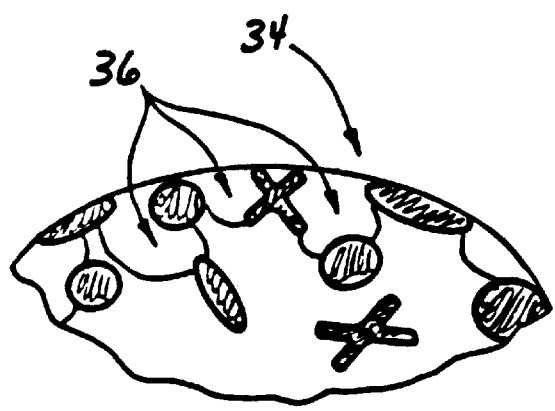
FIG. 4c is an enlargement of FIG. 4b schematically illustrating the surface effects of treatment of the catheter with a solvent.

One way in which the present invention enhances the iontophoretic effect is illustrated in FIGS. 4a–4c. FIG. 4a shows multi-lumen catheter 30 typically used for infusing fluids and made of an iontophoretic combination. If the catheter 30 is extruded with components of the iontophoretic combination-namely Silver (Ag), Platinum (Pt), and Carbon (C) atoms—the polymer matrix wets the surface of these components and a thin film polymer layer exists on the catheter outer surface 34. FIG. 4b is an enlargement of one sidewall 32 of the catheter 30 schematically showing Silver (Ag), Platinum (Pt), and Carbon (C) atoms embedded therein. Application of a solvent in accordance with the teachings of the present invention exposes those iontophoretic atoms closest to the catheter outer surface 34, thus enabling blood to contact these atoms directly, promoting a more efficient galvanic reaction. Moreover, upon closer inspection of the outer surface 34, as seen in the further enlargement of FIG. 4c, a number of cavities, or voids 36 are seen. These voids 36 represent areas in which the polymer matrix between the iontophoretic atoms has been etched or otherwise eroded away. The voids 36 expose iontophoretic atoms deeper into the catheter wall 32 to blood. Thus, a greater surface area of galvanic materials contacts the blood, and the subsequent reaction rate is increased in comparison to a smooth surface. It should be appreciated that the three dimensional, porous surface created by removing part of the polymer matrix in accordance with the present invention increases the yield of silver ions released and prolongs the release of silver ions to enhance the antibacterial effect of the polymer. In addition, the antibacterial effect will begin as soon as the medical device is implanted because of the increased initial exposure (availability) of the active ingredient.

To produce the rough or porous effect on the medical device, the surfaces of the device are treated with a solvent for the polymer matrix under conditions which result in etching and possible swelling of the surface. Whether the surface is merely etched or actually undergoes some swelling due to pore formation are dependent upon the particular solvent used and other parameters including treatment time and temperature, at is only required in accordance with the present invention that sufficient polymer matrix material be removed and/or sufficient pores be formed to expose galvanic metals which otherwise would remain embedded in the polymer matrix.

Alternatively, swelling agents may be used in place of solvents to realize the enhanced iontophoretic effect. Swelling agents may act to disrupt the polymer structure to a degree which facilitates diffusion of the Ag ions into the bloodstream. Indeed, when the catheter walls are very thin, the use of swelling agents may be preferred to avoid potentially compromising the catheter integrity from solvent application. As a general proposition, solvents will cause some swelling, while swelling agents will not necessarily act to etch or dissolve the substrate.

Tetrahydrofuran (TBT) is a preferred reagent for etching and/or swelling the surface of medical devices in accordance with the present invention. THF is preferred because it is an effective solvent for many of the polymers used as the plastic matrix in medical devices. Other suitable polymer solvents include isopropyl alcohol (IPA), dimethylacetamide (DCMA), methylene chloride (MC), methyl ethyl ketone (MEK) or even a combination of these solvents. Suitable swelling agents include ketones, such as acetone, and other suitable expedients known in the art. The particular solvent or swelling agent used to etch/swell the surface of a given medical device will depend upon the particular polymer matrix used in the medical device. Selection of a suitable solvent or solvents for a given polymer matrix can be established by simple experimentation and/or by reference to polymer reference materials well known in the art. For the purposes of this specification, polymer solvents, swelling agents and combinations thereof will be referred to as "exposure enhancement reagents".

The exposure enhancement reagent is contacted with the surface of the medical device for a sufficient time to at least remove a portion of the upper most layer or surface of the polymer to expose the active ingredients located within the underlying polymer matrix. In addition, the contact time between the exposure enhancement reagent may be extended and/or other treatment parameters chosen to allow the exposure enhancement reagent to penetrate deeper into the polymer, interfering with the attractive forces between the polymer strands and pushing them apart in various regions. This creates a swollen, three dimensional, rough or porous region on the surface of the medical device where galvanic metals and/or other active ingredients, which otherwise would remain embedded within the polymer, are exposed. As mentioned, electrolytic physiological fluids that come into contact with the medical device can react with top surface exposed iontophoretic materials and can also fill the voids 36 to react with deeper embedded iontophoretic materials.

The exposure enhancement reagent may be contacted with the polymer in a wide variety of treatment procedures to achieve desired levels of exposure of the embedded active ingredients. For example, the medical device may simply be wiped with an applicator containing the exposure reagent. The exposure reagent is allowed to evaporate or is otherwise removed from the device surface after the desired amount of surface etching/swelling. The device may also be dipped in the exposure enhancement reagent or placed in a spray chamber or other equipment designed to provide contact between the medical device surface and the exposure enhancement reagent under controlled conditions. It is preferred that exposure enhancement reagent penetration be sufficient to provide swelling or etching and swelling.

The temperature of the exposure reagent and exposure reagent/polymer contact times may be varied to achieve different levels of surface etching and polymer matrix penetration. In general, it is preferred to etch and/or swell the device surface a sufficient amount to expose the maximum effective amount of embedded galvanic metals without deleteriously affecting other required properties of the medical device. For example, solvent penetration into the polymer matrix should not be so deep as to reduce the structural strength of the matrix below acceptable limits or increase surface roughness above desired levels. This is important when the polymer body is a coating or is otherwise relatively thin, as discussed above.

For medical devices where the depth of solvent penetration does not need to be limited by other considerations (i.e. relatively large or thick polymer bodies), it is preferred that the additional amount of active ingredients exposed be limited to provide optimum iontophoretic effect during the entire time the medical device is in use. The particular depth of penetration (etching/swelling) will need to be established experimentally for different medical devices to achieve the optimum enhanced iontophoretic affect.

The exposure enhancing reagents of the present invention are intended for use with polymers that are not biodegradable or other wise soluble once they are implanted. Exemplary polymers include any of the non-biodegradable polymers commonly used for making and coating medical implant devices including polyurethanes, such as those marketed under the tradenames TECOFLEX® (a medical grade urethane elastomer), TECOTHANE® (a thermoplastic polyurethane) and PELLETHANE® (a pelletized urethane elastomer). Other suitable polymers are listed below.

Use of Non-Conductive Highly Plasticized Polymers

As mentioned, iontophoretic compounds, such as two dissimilar galvanic materials may be combined in a conductive polymer or a non-conductive polymer loaded with high concentrations of carbon black. In addition, however, non-conductive highly plasticized polymers, such as plasticized polyvinyl chloride (PVC), which have previously not been deemed suitable for iontophoretic use may be made conductive in accordance with the present invention by the addition of ionophoric compounds and/or by incorporating conductive polymers into the matrix. Highly plasticized polymers in comparison to non-plasticized polymers are generally softer, more pliable, and have a lower glass transition temperature. A particularly suitable highly plasticized polymer for use in catheters has a plasticizer content of around 50% and a glass transition temperature between ambient and body temperature. Thus, the catheter is relatively stiff at room temperature to facilitate introduction in the body, but becomes significantly more flexible once its temperature equilibrates with the body temperature. Preferred plasticizers for use in fabricating catheter material suitable for treatment in accordance with the invention include, dioctyladipate, dioctylphalate, epoxidized soybean oil, and others known in the art.

Ionophores are generally defined as chemicals that will carry a specific ion, and are designed to be mobile in plasticized PVCs. In one embodiment, the present invention makes highly plasticized polymers conductive by doping with one or more ionophores. Ionophores chelate with charged species and allow electro-migration of these charged species in neutral lipophilic solutions and gels. A number of ionophoric compounds are available for use in this invention including: metal (e.g. silver/platinum) ionophores such diphenyl sulfide, 6-oxa-3, 9 dithiabicyclo 9.3.I pentadeca 1(15), 11–13 triene or S,S methylenebis (diisobutyldithiocarbamate); halide (e.g. chloride) ionophores such as mesotetraphenylporphorin magnesium chloride; hydrogen or proton ionophores such as tridodecyl amine or 4-nonadecyl pyridine; or electron and general ionophores such as vitamin B12, di tert butyl tartrate, bis triphenylphosphoanylidene ammonium chloride, tetradodecylammonium nitrate or tetraphenylphosphonium tetraphenylborate or, preferably, a combination of these ionophores. A typical application would include adding ca. 0.1–2.0% (by weight) each of a metal, hydrogen, chloride, and electron ionophore from the above list into a standard PVC/plasticizer compound loaded with silver/silver chloride and platinum powders. Some specific examples are given below.

Electrically conductive polymers, on the other hand, directly convey electrons through an otherwise non-conducting media. Their relatively high molecular weight and chain length allows them to facilitate conduction at a distance, even at relatively low concentrations. A number of conductive polymers are available for use in this invention. These polymers include polyaniline alkylsulphonate, poly (4-vinyl N-methyl pyridine) chloride, polyacetylene, polyethylenimine, poly(vinylpyridium methylchloride), fullerenes or a combination of these polymers. Conductivity and silver production of an iontophoretic plasticized polymer, or one which has been doped with an ionophore, can be enhanced with the addition ca. 1–5% of one of the conductive polymers listed above.

Although the above-mentioned techniques make the iontophoretic use of highly plasticized PVC materials possible, the methods can also be applied to non-plasticized polymer mixtures to improve their iontophotetic properties. For example, ionophores may be added to urethane-based materials currently used with iontophoretic dopants to improve the galvanic response.

Anticoagulent Treatment

In accordance with the present invention, the treated iontophoretic-capable polymer is then desirably coated with an anticoagulant, preferably heparin. Heparin may be complexed with quaternary ammonium salts for an additional anticoagulant effect prior to coating the polymer surface. One typical application of heparin is with a solvent carrier solution. In some cases, the solvent in which the heparin is delivered may also be an exposure-enhancing agent for the polymer. In these situations, the time of contact of the solvent with the polymer surface is chosen to preferably cause the etching or swelling effect mentioned above, thus improving the galvanic response of the medical device when brought into contact with the bloodstream. Of course, a separate treatment step with a separate exposure-enhancing agent can also be utilized with the application of a solvent-based heparin complex.

A number of medical grade, non-conductive, non-plasticized polymers are available for use in the present invention. These polymers include polyurethane, polypropylene, and polyethylene. In addition, a number of conductive polymers are also available for use in the present invention. These polymers include polyaniline alkylsulphonate, poly (4-vinyl N-methyl pyridine) chloride, polyacetylene, polyethylenimine, poly(vinylpyridium methylchloride), fullerenes or a combination of these polymers.

Exemplary substances and methods for their manufacture in accordance with the teachings of the present invention are discussed in the following non-limiting examples.

EXAMPLE 1

Polyurethane is loaded with silver, platinum, and carbon black powders and 1–5% w/w poly(4-vinyl N-methyl pyridine) chloride. This mixture is extruded until properly mixed and molded into a single-lumen infusion catheter. The catheter is dipped into enough tetrahydrofuran at room temperature to remove the polymer from the surface of the device and permeate the polymer further to expose the underlying silver, platinum and carbon. Typically, the catheter is dipped for a period lasting from about a few second to a few minutes, depending on the extent of polymer removal desired and how aggressive a chemical is used to dissolve or swell the underlying material, among various factors. For reference purpose, tetrahydrofuran is a fairly aggressive solvent in this regard. The catheter is then wiped with an isopropyl alcohol (w/w 30/40/30) solution. A mixture of quaternary ammonium heparin complex is then dissolved in isopropyl alcohol and deposited onto the surfaces of the catheter.

In use, the single-lumen infusion catheter is inserted through an introducer valve after a catheter has been removed from a hemostasis or Touhy Borst valve to prevent infection and blood clots from developing in the hemostasis valve as a result of blood being left in the valve when a catheter is pulled back through it.

EXAMPLE 2

Plasticized polyvinyl chloride is mixed with silver and platinum powders, and around 0.1–2.0% each of silver diphenyl sulfide, meso-tetraphenylporphorin magnesium chloride, tridodecyl amine and vitamin B12. This mixture is extruded until properly mixed and then formed into flexible extracorporeal tubing. The tubing is dipped into enough methylene chloride to remove the polymer from the surface of the device and permeate the polymer further to expose the underlying silver and platinum and ionophoric compounds.

A mixture of benzalkonium heparin is then dissolved in isopropyl alcohol and deposited onto the surfaces of the tubing.

In use, the tubing is connected to an extracorporeal pump during cardiopulmonary bypass surgery where there is prolonged exposure of the patient's blood to the plastic tubing. The antimicrobial antithrombogenic polymer helps prevent the formation of blood clots or infection in the tubing during surgery.

EXAMPLE 3

Polyurethane is mixed with silver powder, gold powder and carbon black. The mixture is extruded until properly mixed and then coated onto a backform. The backform is dipped into enough tetrahydrofuran to remove the upper most layer of polymer from the surface of the device and permeate the polymer further to expose the underlying silver, gold and carbon. The backform is then used as part of a Multi-Lumen Access Device to prevent infection in the backform.

The polymer may be either extruded or molded to form medical devices including extra-corporal tubing, catheters, obturators, backforms, sheaths, housings and shunts, or as a biocompatibility coating for medical devices including pacers, defibrillators, valves, artificial joints, electrical leads, implantable pumps, plates, and screws.

What is claimed is:

1. A medical device comprising a non-conductive plasticized polymer body, said polymer body comprising at least one iontophoretic compound, said polymer body further comprising an ionophore selected from the group consisting of metal ionophores, halide ionophores, proton ionophores and electron ionophores.

2. The medical device according to claim 1 wherein said polymer body comprises a metal ionophore, a halide ionophore, a proton ionophore and an electron ionophore wherein each of said ionophores is present in an amount of between about 0.1 and 2.0 weight percent of said polymer body.

3. The medical device according to claim 1 wherein said iontophoretic compound is a galvanic metal.

4. The medical device according to claim 1 further comprising the addition of a conductive polymer.

5. The medical device according to claim 4 wherein said conductive polymer is present in an amount of between about 1 to 5 weight percent of said polymer body.

6. The medical device according to claim 1 wherein said polymer body comprises polyvinyl chloride.

7. The medical device according to claim 1 which comprises an anticoagulent attached to said polymer body.

8. The medical device according to claim 7 wherein said anticoagulent comprises heparin.

9. The medical device of claim 1 comprising a surface and a polymer matrix located within said polymer body under said surface and wherein said polymer body is treated with a sufficient amount of an exposure enhancing reagent for a sufficient time to expose at least a portion of an unexposed active ingredients located within said polymer body surface and/or polymer matrix.

10. The medical device of claim 9 wherein said exposure enhancing agent is a solvent for said polymer matrix.

11. The medical device of claim 9 wherein said exposure enhancing agent is a swelling agent.

12. The medical device of claim 9 wherein said exposure enhancing agent is tetrahydrofuran.

13. The medical device of claim 1, wherein the ionophore chelates with a charged species of the iontophoretic compound and allows electro-migration of the charged species in the polymer body.

14. The medical device of claim 1, wherein the ionophore is a metal ionophore selected from the group consisting of:
   diphenyl sulfide;
   6-oxa-3, 9 dithiabicyclo 9.3.1 pentadeca 1(15), 11–13 triene; and
   S,S methylenebis (diisobutyldithiocarbamate).

15. The medical device of claim 1, wherein the ionophore is a halide ionophore consisting essentially of meso-tetraphenylporphorin magnesium chloride.

16. The medical device of claim 1, wherein the ionophore is a proton ionophore selected from the group consisting of:
   tridodecyl amine; and
   4-nonadecyl pyridine.

17. The medical device of claim 1, wherein the ionophore is an electron or general ionophore selected from the group consisting of:
   vitamin B12;
   di tert butyl tartrate;
   bis triphenylphosphoanylidene ammonium chloride;
   tetradodecylammonium nitrate; and
   tetraphenylphosphonium tetraphenylborate.

18. A medical device comprising a non-conductive plasticized polymer body, said polymer body comprising at least one iontophoretic compound, said polymer body further comprising an ionophore selected from the group consisting of metal ionophores, halide ionophores, proton ionophores and electron ionophores, and wherein:
   said polymer body comprises a surface and a polymer matrix located within said polymer body under said surface, wherein at least a portion of the iontophoretic compound is exposed iontophoretic compound which is located at said surface and wherein at least a portion of the iontophoretic compound is unexposed iontophoretic compound which is also located at said surface but within said polymer matrix, said iontophoretic compound further including unexposed iontophoretic compound located deeper within said polymer matrix, wherein the medical device is made by:
   treating said polymer body with a sufficient amount of an exposure enhancing reagent for a sufficient time to expose at least a portion of the unexposed iontophoretic compound located within said polymer body surface and/or polymer matrix.

19. A medical device comprising a non-conductive highly plasticized polymer body, said polymer body comprising at least one iontophoretic compound, said polymer body further comprising a conductive polymer wherein said polymer body has a glass transition temperature between ambient and body temperature.

20. The medical device according to claim 19 wherein said iontophoretic compound is a galvanic metal.

21. The medical device according to claim 19 wherein said polymer body comprises a conductive polymer which is present in an amount of between about 1 to 5 weight percent of said polymer body.

22. The medical device according to claim 19 wherein said polymer body comprises polyvinyl chloride.

* * * * *

UNITED STATES PATENT AND TRADEMARK OFFICE
CERTIFICATE OF CORRECTION

PATENT NO.    : 6,273,875 B1
DATED         : August 14, 2001
INVENTOR(S)   : Jaime Siman et al.

It is certified that error appears in the above-identified patent and that said Letters Patent is hereby corrected as shown below:

<u>Title page,</u>
Item [75], Inventors should read -- Jeff Dove, Jaime Siman, both of Santa Ana, CA --.

Signed and Sealed this

First Day of April, 2003

JAMES E. ROGAN
*Director of the United States Patent and Trademark Office*